United States Patent [19]

Hassel et al.

[11] Patent Number: 4,659,844

[45] Date of Patent: Apr. 21, 1987

[54] CYCLIC ETHERS WHICH ARE SUBSTITUTED IN A α-POSITION BY AN ISOCYANIDE-DICHLORIDE GROUP, AND A PROCESS FOR THEIR PREPARATION

[75] Inventors: Tillmann Hassel, Cologne; Hanns P. Müller, Odenthal-Blecher; Horst Böshagen, Haan, all of Fed. Rep. of Germany

[73] Assignee: Bayer Aktiengesellschaft, Leverkusen, Fed. Rep. of Germany

[21] Appl. No.: 759,033

[22] Filed: Jul. 25, 1985

[30] Foreign Application Priority Data

Aug. 10, 1984 [DE] Fed. Rep. of Germany ....... 3429432

[51] Int. Cl.$^4$ .................. C07D 309/04; C07D 307/22
[52] U.S. Cl. .................................... 549/424; 549/414; 549/415; 549/417; 549/419; 549/472; 549/473; 549/475; 549/476; 549/478; 549/480; 536/22
[58] Field of Search ............. 549/424, 419, 415, 417, 549/414, 472, 473, 475, 476, 478, 480; 536/22

[56] References Cited

U.S. PATENT DOCUMENTS 4,025,622 5/1977 Ogura et al. ...................... 536/22

OTHER PUBLICATIONS

Methoden Der Organischen Chemie, vol. E4, pp. 522-526 (1983).
Industrielle Organische Chemie, 2nd Edition, 1978, p. 172.
Methoden Der Organischen Chemie (Houben-Weyl), vol. V/3 (1962), pp. 623, 631, 632.
Heterocycles, vol. 17 (1982), pp. 87-90, 615, 624, 641.
Chemical Abstracts, vol. 88, 1978, 51125u.
Chemical Abstracts, vol. 80, 1974, 83464e.
Journal of Medicinal Chemistry, vol. 19, No. 2, 1976, pp. 286, 287, and 289.
Collection Szechoslov. Chem. Commun., vol. 29 (1964), pp. 2060-2064, 2068, 2069, 2071, 2072.
Z. Chem. 7. Jg. (1967), vol. 5, pp. 182, 183.

Primary Examiner—Nicky Chan
Attorney, Agent, or Firm—Sprung Horn Kramer & Woods

[57] ABSTRACT

The invention relates to new cyclic ethers which are substituted in the α-position by an isocyanide-dichloride group, of the formula

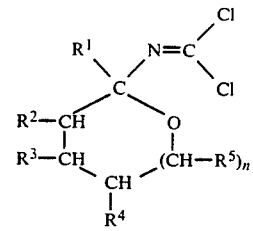

in which $R^1$, $R^2$, $R^3$, $R^4$, $R^5$ and n have the meaning indicated in the description, and to a process for their preparation.

4 Claims, No Drawings

CYCLIC ETHERS WHICH ARE SUBSTITUTED IN A α-POSITION BY AN ISOCYANIDE-DICHLORIDE GROUP, AND A PROCESS FOR THEIR PREPARATION

The invention relates to new cyclic ethers which are substituted in the α-position by an isocyanide-dichloride group, and to a process for their preparation.

New cyclic ethers substituted in the α-position by an isocyanide-dichloride group have been found, of the formula

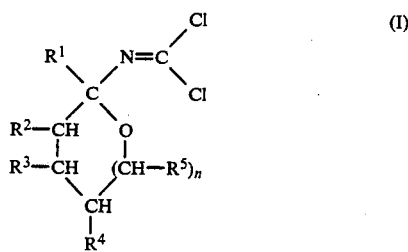

in which
R$^1$ denotes an acyloxymethyl group or—preferably—hydrogen,
n is 0 or 1 and
R$^2$, R$^3$, R$^4$ and R$^5$ independently of one another represent hydrogen, halogen, a nitro, acyloxy or acyloxymethyl group or the radical of a cyclic ether of the formula

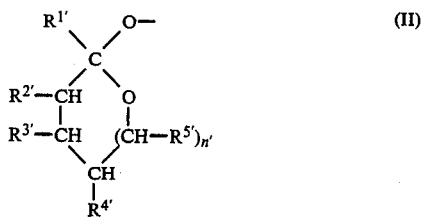

in which
n', R$^{1'}$, R$^{2'}$, R$^{3'}$, R$^{4'}$ and R$^{5'}$, independently of one another and independently of the values n, R$^1$, R$^2$, R$^3$, R$^4$ and R$^5$ in formula I which correspond to them have the meaning indicated for n, R$^1$, R$^2$, R$^3$, R$^4$ and R$^5$ under formula I, subject to the proviso that at least one of the radicals R$^1$, R$^2$, R$^3$, R$^4$ and R$^5$ and at least one of the radicals R$^{1'}$, R$^{2'}$, R$^{3'}$, R$^{4'}$ and R$^{5'}$ is an acyloxymethyl or acyloxy group——and that preferably at least two of the radicals R$^2$, R$^3$, R$^4$ and R$^5$ and at least two of the radicals R$^{2'}$, R$^{3'}$, R$^{4'}$ and R$^{5'}$ are an acyloxymethyl or acyloxy group—and that not more than one of the radicals R$^2$, R$^3$, R$^4$ and R$^5$ and not more than one of the radicals R$^{2'}$, R$^{3'}$, R$^{4'}$, or R$^{5'}$ represents the radical of a cyclic ether of the formula II.

The preferred cyclic ethers of the formula I are acylated (deoxy-) sugars containing an isocyanide-dichloride group attached in the form of a glycoside. Depending on whether one of the radicals R$^2$, R$^3$, R$^4$ or R$^5$ represents the radical of a cyclic ether of the formula II and whether in this formula II in turn one of the radicals R$^{2'}$, R$^{3'}$, R$^{4'}$ or R$^{5'}$ is the radical of a cyclic ether of the formula II, these acylated sugars can be monosaccharides, disaccharides or oligosaccharides. Monosaccharides and disaccharides are particularly preferred, that is to say the cyclic ethers of the formula I which either contain only one radical of the cyclic ether of the formula II or which do not contain said radical.

Cyclic ethers according to the invention which are particularly preferred are those of the formula I in which
R$^1$ is hydrogen and
n is 0 or 1 and
R$^2$, R$^3$, R$^4$ and R$^5$ represent an acyloxy or acyloxymethyl group, or one of the radicals R$^2$, R$^3$, R$^4$ or R$^5$ is the radical of a cyclic ether of the formula II and the remaining radicals R$^2$, R$^3$, R$^4$ and R$^5$ represent an acyloxy or acyloxymethyl group,
R$^{1'}$ in formula II representing hydrogen or an acyloxymethyl group,
n' representing 0 or 1 and
R$^{2'}$, R$^{3'}$, R$^{4'}$ and R$^{5'}$ representing an acyloxy or acyloxymethyl group.

The acyl radicals in the acyloxy and acyloxymethyl groups are preferably derived from the same acid.

The halogen possible for the radicals R$^2$, R$^{2'}$, R$^3$, R$^{3'}$, R$^4$, R$^{4'}$, R$^5$ and R$^{5'}$ is preferably fluorine, chlorine or bromine.

The acyl radicals are preferably derived from lower aliphatic alkanecarboxylic or alkanesulphonic acids, for example C$_1$–C$_8$-alkanecarboxylic or C$_1$–C$_8$-alkanesulphonic acids, such as acetic acid, propionic acid, butyric acid, methanesulphonic acid and ethanesulphonic acid, or from aromatic carboxylic and sulphonic acids, such as benzoic acid and p-toluenesulphonic acid.

Preferred representatives of the acyl radicals are the acyl radicals frequently used in sugar chemistry, such as the methanesulphonyl(mesyl) radical, the p-toluenesulphonic acid (tosyl) radical and, above all, the acetyl radical, which is known as a protective group, and the benzoyl radical.

Examples which may be mentioned of representatives of the preferred cyclic ethers, according to the invention, of the formula I are the following acylated sugars containing an isocyanide-dichloride group attached in the form of a glycoside:

2,3,4,6-Tetraacetyl-D-glucopyranos-1-yl isocyanidedichloride; 2,3,4-tribenzoyl-D-ribopyranos-1-yl isocyanidedichloride; 2,3,5-tribenzoyl-D-ribofuranos-1-yl isocyanidedichloride; 2,2',3,3'4',6,6'-heptaacetyl-D-lactos-1-yl isocyanide-dichloride; 2,2',3,3',4',6,6'-heptaacetyl-D-cellobios-1-yl isocyanide-dichloride; 3-deoxy-3-chloro-2,4,6-triacetyl-D-glucos-1-yl isocyanide-dichloride; 2-deoxy-2-p-toluenesulphonyloxy-3,4,6-triacetyl-D-glucos-1-yl isocyanide-dichloride and also 2,3,4-triacetyl-6-deoxy-6-nitroglucopyranos-1-yl isocyanidedichloride and 2-deoxy-3,4,6-tribenzoyl-D-glucopyranos-1-yl isocyanide-dichloride and 2,3,4-triacetyl-L-arabinopyranosyl isocyanide-dichloride and 2,3,4-triacetyl-D-xylopyranosyl isocyanide-dichloride.

The invention also relates to a process for the preparation of the cyclic ethers of the formula I which are substituted in the α-position by an isocyanidedichloride group; the process is characterised in that cyclic ethers of the formula

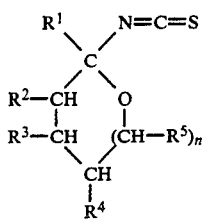

which are substituted in the α-position by an isothiocyanate group and in which n, $R^1$, $R^2$, $R^3$, $R^4$ and $R^5$ have the meaning indicated under formula I are reacted with at least 2 moles of chlorine, preferably 2 to 6 moles and particularly preferentially 2 to 3 moles of chlorine, per mole of isothiocyanate group, in an inert solvent at temperatures from $-40°$ to $+80°$ C., preferably from $-20°$ to $+60°$ C. and particularly preferentially from $0°$ to $+25°$ C.

Surprisingly, the cyclic ethers which are substituted in the α-position by an isocyanide-dichloride group are also obtained in high yields and in a state of great purity if an excess of chlorine is used.

Processes for the preparation of isocyanidedichlorides from isothiocyanates by reaction with chlorine are known (see Houben-Weyl, Methoden der Organischen Chemie ("Methods of Organic Chemistry"), 4th edition, Volume E 4, pages 522 et seq.). It was surprising, however, that this known reaction is also successful with ethers containing acyloxy groups and having an isothiocyanate group present in the α-position, since it would have been expected from Weissermel/Arpe: Industrielle Organische Chemie ("Industrial Organic Chemistry"), 2nd edition, page 172; and from Houben-Weyl, Methoden der Organischen Chemie ("Methods of Organic Chemistry"), 4th edition, Volume V/3, pages 623 et seq., that the chlorination of the acyloxy group would take place preferentially as a competitive reaction.

The process according to the invention may be illustrated by means of the following equation for tetraacetylglucose containing an isothiocyanate group attached in the form of a glycoside:

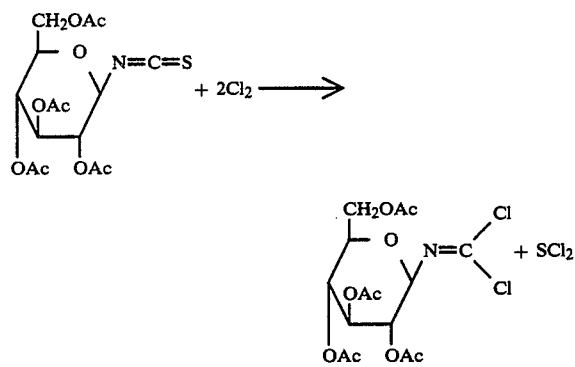

Cyclic ethers which are substituted in the α-position by an isothiocyanate group are known. They are prepared by reacting cyclic ethers which are substituted in α-position by a halogen atom with special thiocyanides of heavy metals; according to Japanese published application No. 77/105,123 silver thiocyanide is used as the heavy metal thiocyanide, in Heterocycles 17, 87 (1982) is described the use of lead thiocyanide. According to the process described in German published application No. 33 41 018 the thiocyanides of alkali metals are used in the presence of phasetransfer catalysts.

The following may be mentioned as examples of representatives of starting compounds which are used preferentially for the preparation of the cyclic ethers, according to the invention, of the formula I: 2,3,4,6-tetraacetyl-D-glucopyranos-1-yl isothiocyanate; 2,3,4-tribenzoyl-D-ribopyranos-1-yl isothiocyanate; 2,3,5-tribenzoyl-D-ribofuranos-1-yl isothiocyanate; 2,2′,3,3′,4′,6,6′-heptaacetyl-D-lactos-1-yl isothiocyanate; 2,2′,3,3′,4′,6,6′-heptaacetyl-D-cellobios-1-yl isothio cyanate; 3-deoxy-3-chloro-2,4,6-triacetyl-D-glucos-1-yl isothiocyanate; 2-deoxy-2-(4-methyl)-phenylsulphonyloxy-3,4,6-triacetyl-D-glucos-1-yl isothiocyanate, and also 2,3,4-triacetyl-6-deoxy-6-nitroglucopyranos-1-yl isothio-cyanate and 2-deoxy-3,4,6-tribenzoyl-D-glucopyranos-1-yl isothiocyanate, 2,3,4-triacetyl-D-xylopyranos-1-yl isothiocyanate.

The process according to the invention can be carried out in the presence of inert solvents, that is to say solvents which remain unchanged under the conditions of the reaction.

Examples of solvents suitable for the process according to the invention are chlorinated aromatic hydrocarbons, such as 1,2-dichlorobenzene or trichlorobenzene; nitrated aromatic hydrocarbons, such as nitrobenzene, and halogenated aliphatic hydrocarbons, such as chloroform, carbon tetrachloride, tetrachloroethane and pentachloroethane; halogenated aliphatic hydrocarbons, in particular chloroform and carbon tetrachloride, are preferred. It is also possible to employ mixtures of the solvents.

The amounts of solvent are, in general, 1 to 20, preferably 2 to 12, parts by weight per part by weight of cyclic ether.

The process according to the invention is, in general, carried out under normal pressure. However, it is also possible to carry out the process according to the invention under a pressure below or above atmospheric pressure (for example within the pressure range from 0.5 to 10 bar). The course of the reaction can be followed by IR spectroscopy (disappearance of the NCS band). In general, the reaction is complete when the 2 moles of $Cl_2$, per mole of NCS group, required for the reaction have been passed in.

The process according to the invention can, for example, be carried out as follows:

The cyclic ether which is substituted in the α-position by an isothiocyanate group is initially taken in the solvent. When the mixture has been brought to the desired reaction temperature, chlorine is passed in with vigorous stirring until the reaction is complete. The solvent and the dichlorosulphane which has been formed are then removed by distillation, and the desired cyclic ether, substituted in the α-position by an isocyanidedichloride group, is isolated from the residue by methods which are in themselves known, for example by recrystallisation.

The cyclic ethers, substituted in the α-position by an isocyanide-dichloride group, of the formula I, in particular the acylated sugars containing an isocyanidedichloride group attached in the form of a glycoside, are valuable intermediate products for the synthesis of biologically active compounds. Thus, for example, their reaction with appropriate acylhydrazines opens up a new economical route for the preparation of 1,3,4- oxadiazoles having an antiviral action (see Acta Pol. Pharm. 1973, 30 (3), pages 255–260; see CA 80, 83,464e); the reaction of the glycosyl isocyanide-dichloride with sodium azide opens up a new, simple route to glycosyl tetrazoles having an antiviral action (see J. Med. Chem. 19 (2), 286 (1976); and the corresponding acylated glycosyl isocyanates are obtained in high yields from the acylated sugars containing an isocyanide-dichloride group attached in the form of a glycoside by reaction with strong acids. These acylated glycosyl isocyanates have hitherto only been obtainable by processes which cannot be used industrially (see Coll. Czech. Chem. Comm. 29 (1969), No. 9, page 2060 and Z. Chemie 7 (1967), No. 5, page 183).

These isocyanates are of great interest because glycosyl ureides having an antibacterial action are obtained from them by reaction with suitable amines (see DE-OS (German Published Specification) No. 2,509,260. The glycosyl isocyanates are also in demand as starting compounds for the synthesis of biologically active heterocyclic N-glycosides, such as are described, for example, in Heterocycles 17, 615 (1983).

EXAMPLE 1

Chlorine is passed at 0° C. into a solution of 192.5 g (0.5 mole) of 2,3,4,6-tetraacetyl-β-D-glucos-1-yl isothiocyanate in 500 ml of chloroform until isothiocyanate can no longer be detected by IR spectroscopy. Chlorine is then passed in again for the same time. The solution is then concentrated to dryness in vacuo. n-Hexane is added to the residue to cause crystallisation. The crystals are taken up in chloroform, and the solution is washed with an aqueous solution of $Na_2CO_3$ and $Na_2SO_3$. After the solution has been dried over $MgSO_4$ and filtered, the solvent is removed.

198 g (≦92.5% of theory) of 2,3,4,6-tetraacetyl-β-D-glucopyranos-1-yl isocyanide-dichloride are obtained; melting point: 122°–123° C.

EXAMPLE 2

Chlorine is passed for 1 hour, at 0° C., into a solution of 10.67 g (15.76 mmoles) of 2,2′,3,3′,4′,6,6′-heptaacetyl-β-D-cellobios-1-yl isothiocyanate in 100 ml of chloroform. The solution is concentrated to dryness. The residue is triturated with 100 ml of n-hexane. The crystals are filtered off with suction and dried.

9.2 g (≦81.5% of theory) of 2,2′,3,3′,4′,6,6′-heptaacetyl-β-D-cellobios-1-yl isocyanide-dichloride are obtained; melting point: 200° C. (decomposition).

EXAMPLE 3

9.2 g (18.3 mmoles) of 2,3,5-tribenzoyl-62 -D-ribofuranos-1-yl isothiocyanate are dissolved in 80 mil of chloroform and chlorinated for 1 hour at 0° C. The solvent and the dichlorosulphane which has been formed are removed. The residue is triturated with 100 ml of n-hexane, in the course of which it crystallises. The crystals are filtered off with suction and dried. 8.9 g (=89.7% of theory) of 2,3,5-tribenzoyl-β-D-ribofuranos-1-yl isocyanide-dichloride are obtained; melting point: 90°–93° C.

EXAMPLE 4

A solution of 5 g (10 mmoles) of 2-deoxy-2-p-toluenesulphonyloxy-3,4,6-triacetyl-β-D-glucopyranos-1-yl isothiocyanate in 20 ml of chloroform is chlorinated at 0° C. After the solvent and the dichlorosulphane have been removed, the residue is dissolved in a little ethyl acetate and is reprecipitated with hexane. After decanting off the solvent and removing the residues of solvent in vacuo, the oil which has been precipitated affords a pale yellow foam which can be converted into an amorphous powder by trituration wih hexane.

4.5 g (=85% of theory) of 2-deoxy-2-p-toluenesulphonyloxy-3,4,6-triacetyl-β-D-glucopyranos-1-yl isocyanide-dichloride are obtained in the form of an amorphous powder.

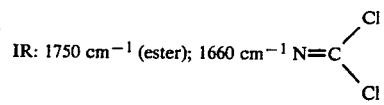

IR: 1750 cm$^{-1}$ (ester); 1660 cm$^{-1}$ N=C$\diagup^{Cl}_{\diagdown Cl}$

EXAMPLE 5

19.25 g (50 mmoles) of 2,3,4,6-tetraacetyl-β-D-glucopyranos-1-yl isothiocyanate are dissolved in 100 ml of carbon tetrachloride and chlorinated as described in Example 1. After the reaction solution has been concentrated, and the residue has been triturated with hexane, 19 g (=98.6% of theory) of 2,3,4,6-tetraacetyl-β-D-glucopyranosyl isocyanide-dichloride are obtained; melting point: 122°–123° C.

If the reaction is carried out in 100 ml of 1,2-dichlorobenzene, instead of carbon tetrachloride, the yield of 2,3,4,6-tetraacetyl-β-D-glucopyranosyl isocyanidedichloride is 92% of theory.

EXAMPLE 6

A solution of 10.4 g (32.9 mmoles) of 2,3,4-tetraacetyl-β-L-arabinopyranos-1-yl isothiocyanate in 100 ml of chloroform is chlorinated as described in Example 1. After the reaction mixture has warmed up to room temperature, the solvent and the dichlorosulphane are removed in vacuo. The residue is taken up in diisopropyl ether, and the solution is stirred with active charcoal and filtered. The diisopropyl ether is removed in vacuo from the filtrate. 9.2 g (78.4% of theory) of 2,3,4-triacetyl-β-L-arabinopyranos-1-yl isocyanide-dichloride are obtained in the form of a highly viscous oil.

EXAMPLE 7

A solution of 2.5 g (7.9 mmoles) of 2,3,4-triacetyl-β-D-xylopyranos-1-yl isothiocyanate in 50 ml of chloroform is chlorinated as described in Example 1. After the solvent and the dichlorosulphane have been removed in vacuo, n-hexane is added to the residue to cause crystallisation. 1.5 g (=53% of theory) of 2,3,4-triacetyl-β-D-xylopyranos-1-yl isocyanide-dichloride are obtained; melting point: 117° C.

Example 8 (use example)

19.2 g (0.2 mole) of methanesulphonic acid is added to a solution of 85.6 g (0.2 mole) of 2,3,4,6-tetraacetyl-β-D-glucopyranos-1-yl isocyanide-dichloride in 400 ml of chlorobenzene. The mixture is heated to 100° C. The reaction is complete after 40 minutes. The solvent and the methanesulphonyl chloride which has been formed are removed by distillation in vacuo. The residue is recrystallised from xylene.

54.6 g (=73% of theory) of 2,3,4,6-tetraacetyl-β-D-glucopyranos-1-yl isocyanate are obtained; melting point 113°–115° C.

EXAMPLE 9 (use example)

A solution of 20.5 g (0.1 mole) of 3,4,-dichlorobenzoylhydrazine in 70 ml of dimethylformamide is added dropwise, in the course of 10 minutes, to a solution, cooled to 0° C., of 42.8 g (0.1 mole) of 2,3,4,6-tetra-O-acetyl-$\beta$-D-glucopyranos-1-yl isocyanide-dichloride and 101 g (1 mole) of triethylamine in 200 ml of dimethylformamide. The mixture is stirred for 15 minutes at room temperature and filtered with suction and the filtrate is concentrated. The residue is taken up in chloroform and washed with water. The chloroform phase is dried and concentrated. The product is recrystallised from ethanol.

28.5 g (=50.7% of theory) of 2-(3,4-dichlorophenyl)-5-(2,3,4,6-tetra-O-acetyl-$\beta$-D-glucopyranosyl)-amino-1,3,4-oxadiazole are obtained; melting point: 180°–181° C.

EXAMPLE 10 (use example)

3.035 g (0.0467 mole) of sodium azide are added to a solution of 20 g (0.0467 mole) of 2,3,4,6-tetra-O-acetyl-$\beta$-D-glucopyranos-1-yl isocyanide-dichloride in 150 ml of dimethylformamide, and the mixture is stirred for 30 minutes. The mixture is filtered with suction, the filtrate is concentrated and the resulting syrup is recrystallised from ethanol. 10 g (50% of theory) of 1-(2,3,4,6-tetra-O-acetyl-$\beta$-D-glucopyranosyl)-5-chlorotetrazole are obtained; melting point 172° C.

What is claimed is:

1. A cyclic ether, substituted in the $\alpha$-position by an isocyanide-dichloride group, of the formula

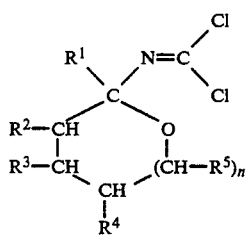

in which $R^1$ is alkanoyloxymethyl, alkanesulfonyloxymethyl, benzoyloxymethyl or tolylsulfonyloxymethyl or hydrogen, n is 0 or 1 and $R^2$, $R^3$, $R^4$ and $R^5$ independently of one another are hydrogen, halogen, nitro, alkanoyloxy, alkansulfonyloxy, benzoyloxy, tolylsulfonyloxy, alkanoyloxymethyl, alkanesulfonyloxymethyl, benzoyloxymethyl or tolylsulfonyloxymethyl or the radical of a cyclic ether of the formula

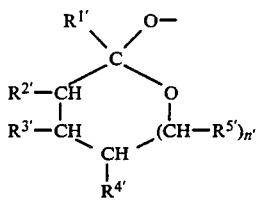

in which $n'$, $R^{1'}$, $R^{2'}$, $R^{3'}$, $R^{4'}$ and $R^{5'}$, independently of one another and independently of the values n, $R^1$, $R^2$, $R^3$, $R^4$ and $R^5$ in the formula I which correspond to them have the meaning indicated for n, $R^1$, $R^2$, $R^3$, $R^4$ and $R^5$ under formula I, subject to the proviso that at least one of the radicals $R^1$, $R^2$, $R^3$, $R^4$ and $R^5$ and at least one of the radicals $R^{1'}$, $R^{2'}$, $R^{3'}$, $R^{4'}$ and $R^{5'}$ is alkanoyloxy, alkansulfonyloxy, benzoyloxy, tolylsulfonyloxy alkanoyloxymethy, alkanesulfonyloxymethyl, benzoyloxymethyl or tolylsulfonyloxymethyl and that not more than one of the radicals $R^2$, $R^3$, $R^4$ or $R^5$ and none of the radicals $R^{2'}$, $R^{3'}$, $R^{4'}$ or $R^{5'}$ represent the radical of a cyclic ether of the formula II.

2. A cyclic ether according to claim 1, wherein in formula I, $R^1$ is hydrogen and n is 0 or 1 and at least two of the radicals $R^1$, $R^2$, $R^3$, $R^4$ and $R^5$ and at least two of the radicals $R^{1'}$, $R^{2'}$, $R^{3'}$, $R^{4'}$ and $R^{5'}$ are alkanoyloxy, alkansulfonyloxy, benzoyloxy, tolylsulfonyloxy, alkanoyloxymethyl, alkanesulfonyloxymethyl, benzoyloxymethyl or tolylsulfonyloxymethyl.

3. A cyclic ether according to claim 1, wherein in formula I, $R^1$ is hydrogen and n is 0 or 1 and $R^2$, $R^3$, $R^4$ and $R^5$ are alkanoyloxy, alkansulfonyloxy, benzoyloxy, tolylsulfonyloxy, alkanoyloxmethyl, alkanesulfonyloxymethyl, benzoyloxymethyl or tolylsulfonyloxymethyl, or one of the radicals $R^2$, $R^3$, $R^4$ or $R^5$ is the radical of a cyclic ether of the formula II, and the remaining radicals $R^2$, $R^3$, $R^4$ and $R^5$ are alkanoyloxy, alkansulfonyloxy, benzoyloxy, tolylsulfonyloxy, alkanoyloxymethyl, alkanesulfonyloxymethyl, benzoyloxymethyl or tolylsulfonyloxymethyl, and, in formula II, $R^{1'}$ is hydrogen or alkanoyloxymethyl, alkanesulfonyloxymethyl, benzoyloxymethyl or tolylsulfonyloxymethyl, n' is 0 or 1 and $R^{2'}$, $R^{3'}$, $R^{4'}$ and $R^{5'}$ are alkanoyloxy, alkanesulfonyloxy, benzoyloxy, tolylsulfonyloxy, alkanoyloxymethyl, alkansulfonyloxymethyl, benzoyloxymethyl or tolylsulfonyloxymethyl.

4. A cyclic ether according to claim 1, wherein $R^1$, $R^2$, $R^3$, $R^4$, $R^5$, $R^{1'}$, $R^{2'}$, $R^{3'}$, $R^{4'}$ and $R^{5'}$ are alkanoyloxy, benzoyloxy, alkanoyloxymethyl or benzoyloxymethyl groups which are derived from $C_1$–$C_8$-alkanecarboxylic acids or benzoic acid.

* * * * *

UNITED STATES PATENT AND TRADEMARK OFFICE
CERTIFICATE OF CORRECTION

PATENT NO. : 4,659,844

DATED : April 21, 1987

INVENTOR(S) : Tillmann Hassel, et al.

It is certified that error appears in the above-identified patent and that said Letters Patent is hereby corrected as shown below:

| | |
|---|---|
| Col. 4, line 20 | After "triacetyl-" insert --L-arabinopyranos-1-yl isothiocyanate and 2,3,4-triacetyl- -- |
| Col. 5, lines 36, 47 | Delete " $\stackrel{\angle}{=}$ " and substitute --$\underline{\alpha}$-- |
| Col. 5, line 52 | Delete "62" and substitute --ß-- |
| Col. 5, line 53 | Delete "mil" and substitute --ml-- |
| Col. 6, line 6 | Correct spelling of --with-- |
| Col. 8, line 20 | Delete "R5" and substitute --$R^{5'}$-- |

Signed and Sealed this

Twenty-ninth Day of December, 1987

Attest:

DONALD J. QUIGG

Attesting Officer    Commissioner of Patents and Trademarks